United States Patent
Vallana et al.

(10) Patent No.: US 6,645,243 B2
(45) Date of Patent: Nov. 11, 2003

(54) STENT FOR ANGIOPLASTY AND A PRODUCTION PROCESS THEREFOR

(75) Inventors: Franco Vallana, Turin (IT); Benito Chinaglia, Turin (IT); Maria Curcio, Saluggia (IT); Giovanni Rolando, Chivasso (IT)

(73) Assignee: Sorin Biomedica Cardio S.p.A., Saluggia (IT)

( * ) Notice: Subject to any disclaimer, the term of this patent is extended or adjusted under 35 U.S.C. 154(b) by 0 days.

(21) Appl. No.: 09/004,376

(22) Filed: Jan. 8, 1998

(65) Prior Publication Data

US 2003/0135254 A1 Jul. 17, 2003

(30) Foreign Application Priority Data

Jan. 9, 1997 (IT) .......................................... TO97A0012

(51) Int. Cl.$^7$ .............................. A61F 2/06; A61N 5/00
(52) U.S. Cl. ................... 623/1.46; 623/1.15; 623/1.44; 600/3
(58) Field of Search ................... 623/1.1, 1.15, 623/1.34, 1.42, 1.44, 1.45, 1.46; 600/3

(56) References Cited

U.S. PATENT DOCUMENTS

| | | | |
|---|---|---|---|
| 4,349,498 A | * 9/1982 | Ellis et al. ...................... 264/81 |
| 4,503,569 A | 3/1985 | Dotter |
| 4,768,507 A | 9/1988 | Fischell et al. |
| 4,776,337 A | 10/1988 | Palmaz |
| 4,800,882 A | 1/1989 | Gianturco |
| 4,830,003 A | 5/1989 | Wolff et al. |
| 4,856,516 A | 8/1989 | Hillstead |
| 4,886,062 A | 12/1989 | Wiktor |
| 4,907,336 A | 3/1990 | Gianturco |
| 5,059,166 A | * 10/1991 | Fischell et al. ................ 600/3 |
| 5,342,283 A | * 8/1994 | Good ............................ 600/8 |
| 5,449,373 A | 9/1995 | Pinchasik et al. |
| 5,632,771 A | * 5/1997 | Boatman et al. ............ 623/1.34 |
| 5,707,332 A | * 1/1998 | Weinberger ..................... 600/3 |
| 5,713,828 A | * 2/1998 | Coniglione ..................... 600/7 |
| 5,871,437 A | * 2/1999 | Alt ................................ 600/3 |
| 5,891,191 A | * 4/1999 | Stinson ......................... 623/1 |
| 6,146,322 A | * 11/2000 | Papirov et al. ................ 600/3 |
| 6,159,142 A | * 12/2000 | Alt ................................ 600/3 |
| 6,419,621 B1 | * 7/2002 | Sioshansi et al. ............. 600/3 |

FOREIGN PATENT DOCUMENTS

| | | | |
|---|---|---|---|
| EP | 0433011 | * 6/1991 | ................... 623/1 |
| EP | 0 540 290 A2 | 10/1992 | |
| WO | WO 96/03092 A1 | 2/1996 | |

OTHER PUBLICATIONS

T. A. Fischell, "Radioactive Stents for the Prevention of Neointimal Hyperplasia", *Physician's Press "The new manual of interventional cardiology"*, chapter 18, p. 134 ss (1996).

R. Makkar et al., "Technical and Engineering Aspects of Stents Which May be Either Permanent or Removable", *Endoluminal Stenting*, chapter 32, p. 230 (1996).

E. J. Topel, (ed.), "Coronary Stenting", *Textbook of Interventional Cardiology*, Sec. IV of vol. 11 (1994).

* cited by examiner

Primary Examiner—Corrine McDermott
Assistant Examiner—Alvin Stewart
(74) Attorney, Agent, or Firm—Popovich & Wiles, P.A.

(57) ABSTRACT

The stent for angioplasty has a body in the form of a generally tubular casing capable of being dilated in use from a radially-contracted position to a radially-expanded position. The body includes a support structure made from a first material capable of withstanding this dilation without losing its structural integrity. A structure made from a second material which has been rendered radioactive following the exposure of the stent itself to a neutron flux is associated with at least a portion of the carrying structure.

12 Claims, 3 Drawing Sheets

STENT FOR ANGIOPLASTY AND A PRODUCTION PROCESS THEREFOR

FIELD OF THE INVENTION

The present invention generally concerns so-called stents for angioplasty.

BACKGROUND OF THE INVENTION

The term "stent" is intended generally to indicate devices intended for endoluminal application (for example, within a blood vessel) usually effected by catheterisation, with the subsequent expansion in place for the local support of the lumen. The principal aim of this is to avoid the re-establishment of a stenotic site at the treated site. It should be noted that the use of substantially similar structures to effect the expansion and anchorage in place of vascular grafts has already been proposed in the art: naturally, this possible extension of the field of application should also be seen as being included within the ambit of the invention.

For a general review of vascular stents, reference may usefully be made to the work "Textbook of Interventional Cardiology" edited by Eric J. Topol, W. B. Saunders Company, 1994 and, in particular, to section IV of volume II, entitled "Coronary stenting".

Many patent documents have addressed this problem, such as, for example, U.S. Pat. No. 4,776,337, U.S. Pat. No. 4,800,882, U.S. Pat. No. 4,907,336, U.S. Pat. No. 4,886,062, U.S. Pat. No. 4,830,003, U.S. Pat. No. 4,856,516, U.S. Pat. No. 4,768,507, and U.S. Pat. No. 4,503,569.

One problem that is not yet completely resolved in connection with the implantation of a stent is in relation to restenosis which, depending on the type of lumen in question, may be more or less likely to occur. Several studies have shown that the principal mechanism causing restenosis after the stent-implantation operation is a hyperplasia of the neointima mediated by the cells of the smooth muscle.

It has, however, been noted that nuclear radiation, in particular β-radiation, inhibits the formation of the neointima. The manufacture of a stent capable of emitting nuclear radiation has therefore already been proposed: in this way, after implantation, the surrounding tissues become irradiated, which inhibits the above-mentioned hyperplasia.

To this end, atoms of the $P^{32}$ radionuclide are injected, by means of a cyclotron, onto the surface of a stent made from conventional material, for example, stainless steel, before it is implanted (see "Radioactive Stents for the Prevention of Neointimal Hyperplasia" by Tim A. Fischell, from "Endoluminal Stenting" chapter 18, p. 134 (1996) edited by W. B. Saunders Company Ltd).

According to a similar technique (see "Technical and Engineering Aspects of Stents Which May Be Either Permanent or Removable" by R. Makkar et al., from "Endoluminal Stenting", chapter 32, p. 230, (1996) edited by W. B. Saunders Company Ltd), a titanium stent is bombarded with protons having an energy equal to 8 MeV, which provoke the reaction $Ti^{48}(p,n)V^{48}$, also leading in this case to the formation of a radioactive nuclide.

These methods require the use of very complicated equipment, such as a cyclotron, for accelerating the charged particles. In addition, since these particles are retained on the surface layer of the stent body, a sophisticated system must be provided for moving the latter in order to expose as much as possible of its surface to the particle beam.

Overall, therefore, these known techniques, although valid for research, are not suited to the mass production of radioactive stents.

SUMMARY OF THE INVENTION

The object of the present invention is that of overcoming the aforesaid disadvantages, and the invention has the characteristics referred to specifically in the claims.

In one aspect, the invention is a stent for angioplasty having a body in the form of a generally tubular casing capable of being dilated in use from a radially-contracted position to a radially-expanded position, the body comprising a support structure of a first material capable of withstanding dilation without losing its structural integrity, and having associated with at least a part of the support structure a structure made from a second material which is made radioactive following the exposure of the stent to a neutron flux.

The structure made from the second material may comprise a continuous layer on at least a portion of the support structure or on the entire support structure. The continuous layer may range in thickness between 0.4 and 1 micrometer.

In a preferred embodiment, the structure made from the second material forms a core within the support structure. The core may have a diameter of between 10 and 100 micrometers.

In another preferred embodiment, the structure made from the second material is in the form of a plurality of inserts housed in associated recesses formed on the surface of the support structure.

The second material may be iridium, tantalum or mixtures thereof.

In another aspect, this invention is a method for the production of a stent having a body in the form of a generally tubular casing capable of being dilated in use from a radially-contracted position to a radially-expanded position, the body comprising a support structure of a first material capable of withstanding dilation without losing its structural integrity, and having associated with at least a part of the support structure a structure made from a second material which is radioactivatable, wherein the body is exposed to a neutron flux so as to render the second material radioactive.

The body may further comprise a carbon film.

The association of the second structure with the support structure may be achieved by means of galvanic techniques or sputtering, by coextrusion, or by welding, mounting or inclusion.

In yet another aspect, this invention is an intermediate product obtainable by the method for the production of a stent having a body in the form of a generally tubular casing capable of being dilated in use from a radially-contracted position to a radially-expanded position, the body comprising a support structure of a first material capable of withstanding dilation without losing its structural integrity, and having associated with at least a part of the support structure a structure made from a second material which is radioactivatable, wherein the body is exposed to a neutron flux so as to render the second material radioactive.

BRIEF DESCRIPTION OF THE DRAWING

Further advantages and characteristics of the present invention will become clear from the following detailed description given by way of non-limitative example and with reference to the accompanying figures, in which.

DETAILED DESCRIPTION OF THE PREFERRED EMBODIMENTS

In the stent of the invention, the properties of the two different materials from which they are formed are exploited to best advantage: in particular, the first material gives the stent the desired mechanical properties and structural strength, while the second material enables the emission of nuclear radiation with the aforesaid advantages relating to the effect of inhibiting the formation of the neointima.

The materials conventionally used for stent production may be used as a first material, for example, stainless steel, while tantalum, iridium and mixtures thereof are preferred as the second material.

The choice of second material may be dictated by considerations of its compatibility with the first material, by the size of the desired activation section, and by the characteristics of the radionuclide which forms following exposure to the neutron flux.

The basic technique for the manufacture of this stent constitutes a factor which is in itself non-influential in the context of the invention, which is applicable irrespective of whether the stents are formed from a wire or a microtube.

Achieving the radioactivation of the second material by means of neutrons has significant operative advantages when compared with the known methods which require the use of charged particles.

In the first instance, the neutrons are generated in conventional fission reactors which are more widespread and easily understood than particle accelerators. These reactors also produce very high neutron fluxes (up to $10^{14}$ n/cm$^2 \cdot$s), so that the radioactivation can be achieved in a very short time period.

Secondly, unlike charged particles, neutrons are not actually absorbed by the materials ordinarily used for the body of the stent. Therefore, the radioactivation treatment according to the invention can be effected without turning or otherwise moving the stent, but simply by exposing it to the neutron flux which is capable of activating even the portions of the second material not directly exposed to it after having passed through portions of the first material.

Figure 1:
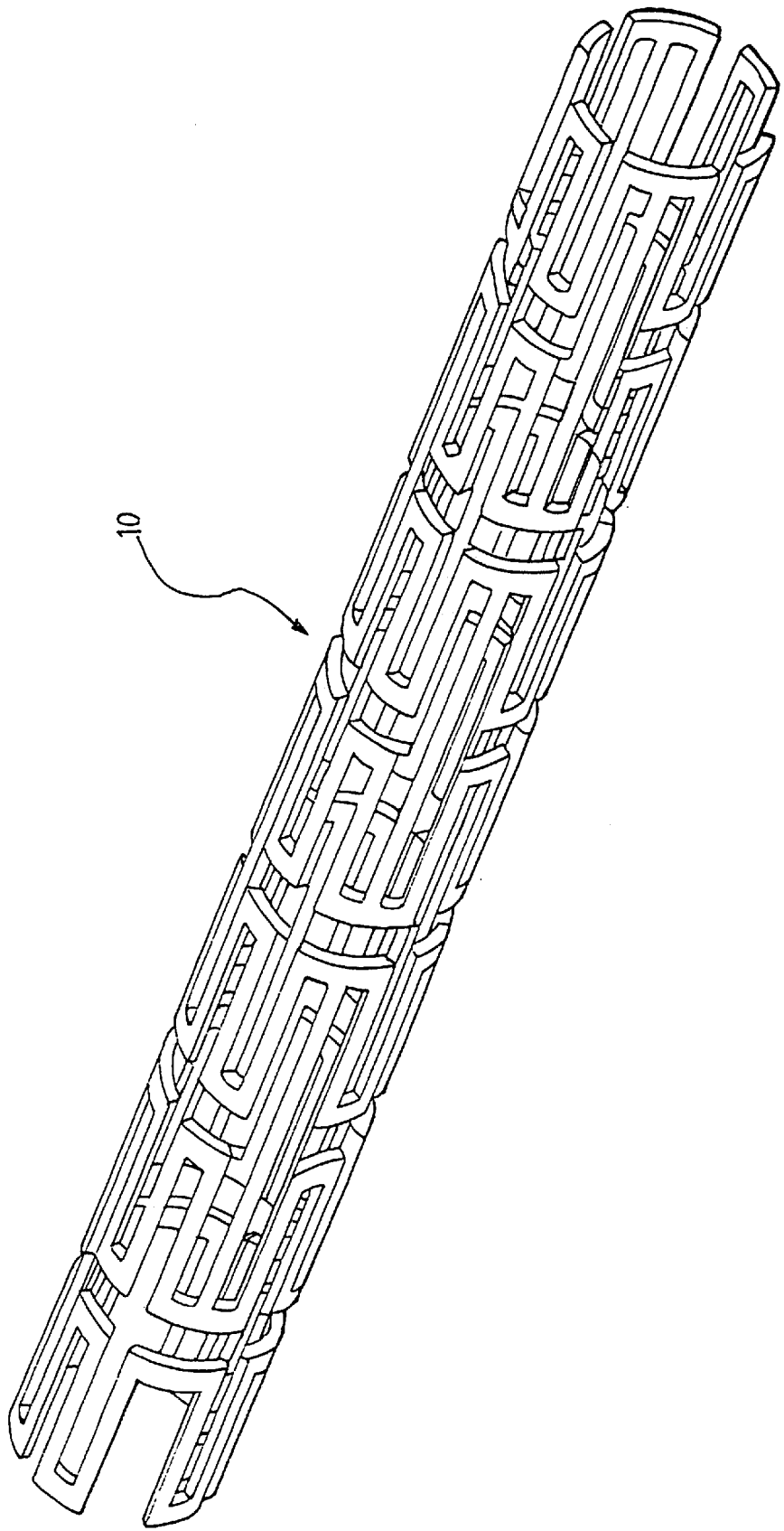
FIG. 1 is a general perspective view of a stent formed according to the invention.
Figure 2:
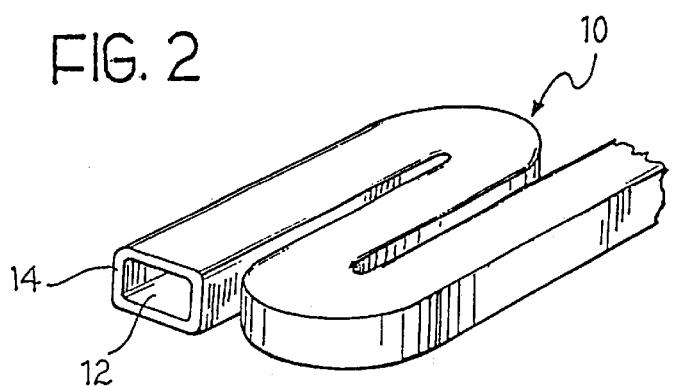
FIG. 2 is a view on an enlarged scale of a detail of FIG. 1.

A stent (FIG. 1) has a body 10 comprising a generally tubular casing with a wall having a looped or mesh-like apertured structure, an example of which can be seen on an enlarged scale in FIG. 2. The body 10 is capable of being dilated in use from a radially-contracted position to a radially-expanded position. It includes (FIG. 2) a support structure 12 made of a first material capable of withstanding this dilation without losing its structural integrity. The support structure 12, for example, made from AISI 316 L steel, is obtained from a microtube that is subsequently subjected to an operation for cutting the apertures, using known methods which form the subject of a fairly extensive body of literature and which do not therefore require detailed description in this context.

A layer 14 of Ta of a thickness equal to approximately 1/100 of the thickness of the body, which is usually between 0.07 and 0.1 mm, is deposited over the entire outer surface of the support structure 12. The layer 14 may, for example, be deposited using a PVD (Physical Vapour Deposition) process effected under vacuum with sputtering apparatus or using galvanic techniques.

Therefore, by exposing the coated stent to a neutron flux, for example, within a fission reactor, radioactive nuclides are generated, principally in relation to the tantalum nuclei according to the reaction Ta$^{181}$(n,γ)Ta$^{182}$.

Similar reactions also take place in relation to the Fe$^{58}$ and Cr$^{50}$ nuclei present in the steel of the support structure, leading to the formation of the radioactive nuclides Fe$^{59}$ and Cr$^{51}$, although to a lesser extent than for tantalum.

The equation which expresses the variation over time of the activity of a given radio-isotope (expressed as the number of disintegrations per unit of time) is as follows:

$$A_i = \frac{m_i p_i}{M_i} N \cdot \sigma_i \Phi (1 - e^{-\lambda_i t1}) e^{-\lambda_i t2}$$

in which:

$A_i$=the activity (disintegrations/sec) of the radionuclide
$p_i$=isotopic percentage
$m_i$=mass of the element i(g)
$M_i$=atomic mass
N=Avogadro's number
$\sigma_i$=cross section (cm$^2$)
$\Phi$=neutron flux (n/cm$^2 \cdot$s)
$\lambda_i$=decay constant=0.693 T$_{1/2}$
$t_1$=time of irradiation
$t_2$=time since the end of the irradiation.

Figure 3:
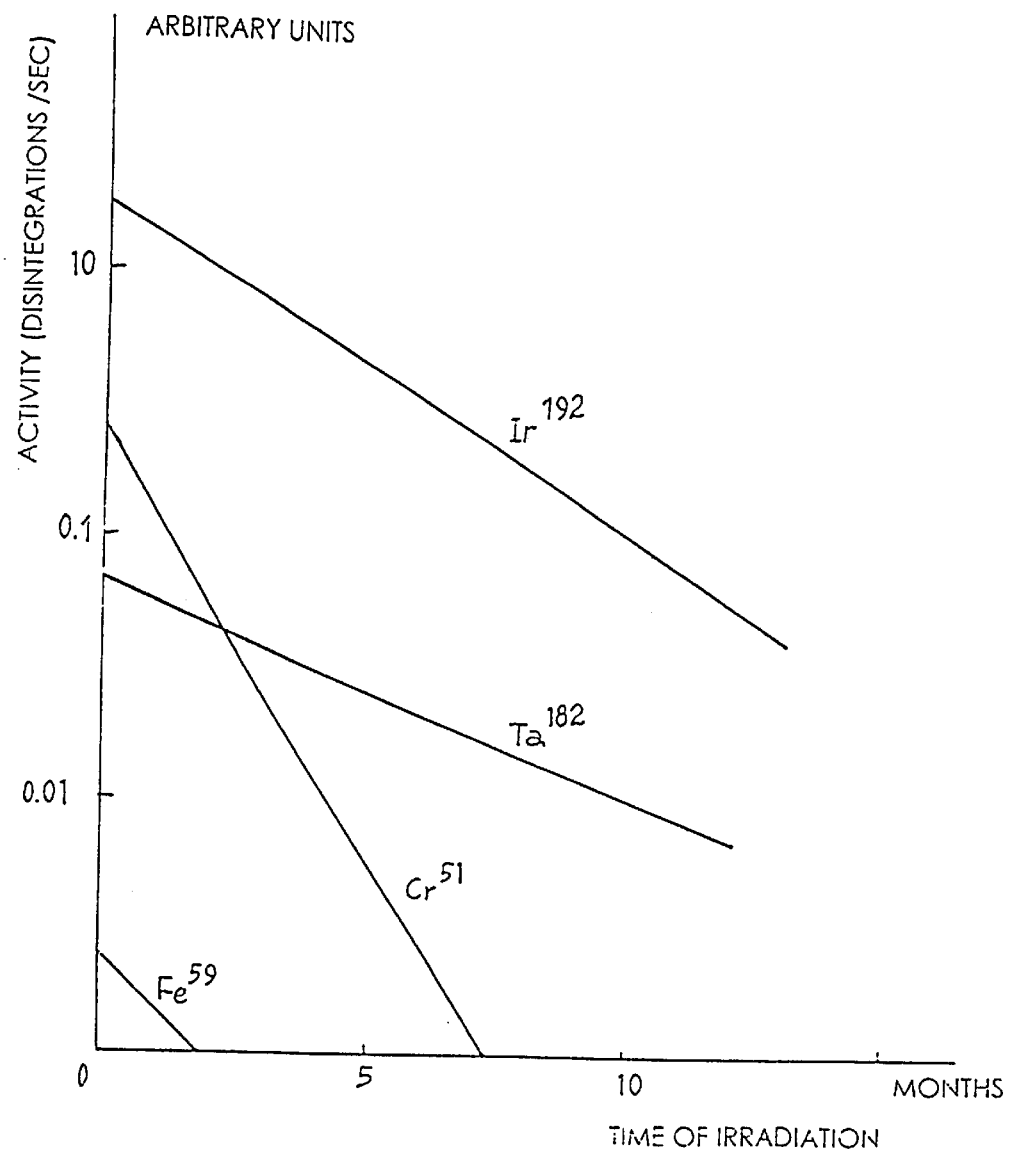
FIG. 3 is a diagram on a logarithmic scale which shows the activity of several radionuclides as a function of the time elapsed since their activation.

By utilising this equation, the graph shown in FIG. 3 is obtained, which shows the variation in the activity (expressed in arbitrary units) of the main radionuclides (Fe$^{59}$, Cr$^{51}$, Ta$^{182}$) which form following the neutron irradiation of a stent of the type described above, as a function of the time elapsed since the irradiation.

It should be noted that, after several months, the only significant activity is that of the Ta$^{182}$ which emits β radiation of maximum energy equal to 0.43 MeV and has a half life of 112 days. This medium energy and low-duration radiation is particularly suitable for inhibiting restenosis.

From the knowledge of the patterns of decay of the type shown in FIG. 3, and the optimal value for the medical applications of radioactive activity, it is therefore possible to determine the most favourable moment for the implantation of a stent that has been subjected to the radioactivation treatment described above.

When waiting for the appropriate moment, the stent can be subjected to other operations such as being coated with a highly biocompatible carbon film or, if not done previously, packaging and sterilisation.

By repeating the operations described above, but replacing the layer of tantalum with a 1 μm thick layer of iridium, a radioactive stent is obtained following the formation of the radionuclide Ir$^{192}$, whose variation in activity over time can be determined by considering the related line in FIG. 3.

Ir$^{192}$ also emits β radiation, although of much greater energy (0.68 MeV), and with a shorter half life (74.5 days) than the Ta$^{182}$. Utilising iridium enables a greater depth of penetration by the radiation over a shorter period of time to be achieved.

Figure 4:
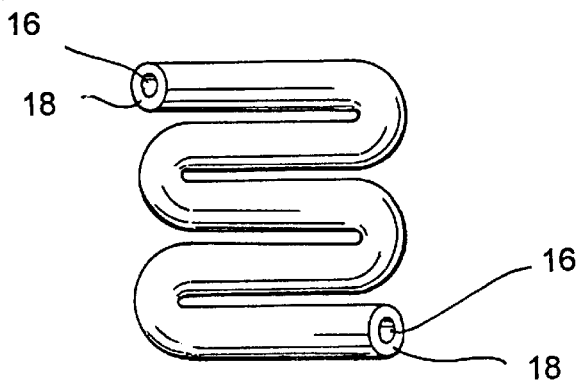
FIG. 4 is a view of a detail of a stent according to a different embodiment of the invention.

FIG. 4 illustrates a wire utilisable with known techniques for the production of a stent having properties similar to that described above. In this case also, it has internal support structure 16 made from AISI 316 L steel, which may be coated, for example, using sputtering or galvanic techniques, with a layer 18 of tantalum or iridium which is subsequently radioactivated by operations similar to those described above.

According to the invention, it is also possible to reverse the positions of the support structure and the radioactive structure in the wire, so that this latter is positioned on the inside. A wire of this type can, for example, be formed using coextrusion techniques of the DFT (Drawn Fillet Tubing) type.

Figure 5:
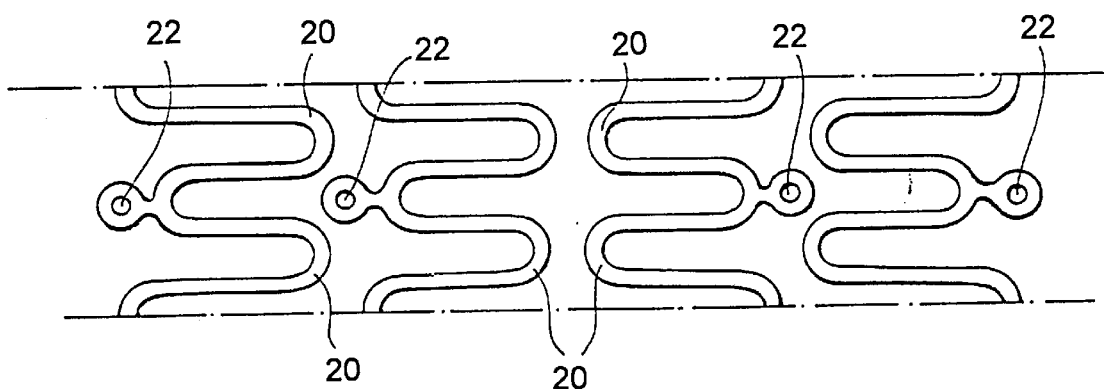
FIG. 5 is a view of a detail of a stent according to a further embodiment of the invention.

FIG. 5 shows a further embodiment of the present invention. In this case, structure 22 of the second radioactivatable material is made in the form of a plurality of inserts housed in respective recesses formed on the surface of support structure 20. The inserts can be attached to support structure 20 using known techniques of welding, mounting, inclusion and the like.

Naturally, it is understood that while the principle of the invention remains the same, the details of manufacture and the embodiments may be widely varied with respect to those described above, without by this departing from the ambit of the present invention.

What is claimed is:

1. A method for inhibiting restenosis in a lumen of a vessel comprising:

providing a stent formed from a first material, the stent having a body in the form of a substantially tubular casing capable of being dilated in use from a radially-contracted position to a radially-expanded position;

coating the stent with a second material capable of being made radioactive;

exposing the coated stent to a neutron flux so that the second material becomes radioactive;

determining an optimal radiation level for inhibiting restenosis in the lumen of the vessel;

implanting the exposed coated stent in the lumen of the vessel at a predetermined time after the exposing step, the predetermined time being selected such that the level of radioactivity of the second material has decayed to the optimal radiation level.

2. The method according to claim 1, wherein the coating step is done by one of galvanic techniques and sputtering.

3. The method according to claim 1, wherein the coating step is done by means of coextrusion.

4. The method according to claim 3, wherein the coextrusion forms a core of the second material within the first material.

5. The method according to claim 4, wherein the core has a diameter ranging from about 10 to about 100 micrometers.

6. The method according to claim 1, wherein the step of coating the stent with the second material is done by one of welding, mounting and inclusion.

7. The method according to claim 1, wherein the step of coating comprises coating a continuous layer of the second material on the stent.

8. The method according to claim 7, wherein the continuous layer is selected from iridium, tantalum, and mixtures thereof.

9. The method according to claim 7, wherein the continuous layer has a thickness between 0.4 and 1 micrometers.

10. The method according to claim 1 wherein the level of radioactivity is a result of beta radiation.

11. The method according to claim 1 wherein the second material is iridium 191.

12. The method according to claim 1 wherein the second material is tantalum 181.

* * * * *